US007576049B2

(12) United States Patent
Shaath et al.

(10) Patent No.: US 7,576,049 B2
(45) Date of Patent: Aug. 18, 2009

(54) SOLVENT BASED PLANT EXTRACTS

(75) Inventors: Nadim A. Shaath, Elmsford, NY (US); Peter Matravers, Minnetonka, MN (US); Timothy Roland Kapsner, Minneapolis, MN (US); Alaa Hashem, Cairo (EG); Ko-ichi Shiozawa, Shoreview, MN (US)

(73) Assignee: Aveda Corporation, Blaine, MN (US)

( * ) Notice: Subject to any disclaimer, the term of this patent is extended or adjusted under 35 U.S.C. 154(b) by 476 days.

(21) Appl. No.: 11/158,105

(22) Filed: Jun. 21, 2005

(65) Prior Publication Data

US 2006/0003036 A1 Jan. 5, 2006

Related U.S. Application Data

(60) Provisional application No. 60/581,484, filed on Jun. 21, 2004.

(51) Int. Cl.
*A61K 8/00* (2006.01)

(52) U.S. Cl. .......................................................... 512/5

(58) Field of Classification Search ...................... 512/5
See application file for complete search history.

(56) References Cited

U.S. PATENT DOCUMENTS

| | | | | |
|---|---|---|---|---|
| 5,235,021 | A | 8/1993 | Chum et al. | |
| 6,022,573 | A | 2/2000 | Hagiwara | |
| 6,406,720 | B1 | 6/2002 | Pauly et al. | |
| 2003/0118678 | A1* | 6/2003 | Teng et al. | 424/774 |
| 2004/0105899 | A1 | 6/2004 | Dowdle et al. | |
| 2005/0208155 | A1 | 9/2005 | Teng et al. | |

FOREIGN PATENT DOCUMENTS

| | | | |
|---|---|---|---|
| GB | 2341858 | * | 3/2000 |
| JP | 61-36257 A | | 2/1986 |
| JP | 2004/075638 | * | 3/2004 |
| JP | 2004/091379 | * | 3/2004 |

OTHER PUBLICATIONS

Supplementary European Search Report; EP05762422.3; Completion Date: Jun. 8, 2009; Date of Mailing: Jun. 17, 2009.

* cited by examiner

*Primary Examiner*—John R Hardee
(74) *Attorney, Agent, or Firm*—Yongzhi Yang

(57) ABSTRACT

The present invention relates to a method for producing petrochemical-free aroma components, which comprises extracting aroma components from plant materials with a volatile ester such as ethyl acetate. The method produces unique concrete, wax and absolute components that are useful in all types of fragranced compositions, which compositions, due to the absence of petrochemicals, can be certified as organic.

2 Claims, No Drawings

SOLVENT BASED PLANT EXTRACTS

The following invention claims priority under 35 USC 119e of U.S. provisional application 60/581,484 filed Jun. 21, 2004.

FIELD OF THE INVENTION

The invention relates to methods for the production of natural aroma components, and the aroma components prepared by these methods.

BACKGROUND OF THE INVENTION

The use of fragrance by mankind as an attractant to the opposite sex has been known for hundreds of years, and in modern time the variety of fragrances available commercially has been growing in leaps and bounds for many years. Fragrance has now also become not only an accompaniment to one's person, but also to one's home or office environment. The concept that one's mood can be altered or improved by exposure to certain fragrances has been around for many years, and in recent times, there are even scientific tests which confirm this psychological power of fragrance.

It is generally recognized in the fragrance industry that natural fragrances are preferable to synthetic ones. It is in many cases possible by chemical analysis, to break down a fragrance, for example, strawberry or rose, into its constituent components, and then synthetically prepare one or more of those components in an attempt to reproduce the aroma of the original source. However, the resulting synthetic products frequently lack the "essence" of the original natural product, and are normally considered inferior in quality to the natural source. Unfortunately, the preparation of aroma compounds from natural sources is not a simple matter, and can be very costly, not always itself yielding products of optimum quality.

Natural fragrances are typically derived from plant extracts. A majority of the aromatic components of plant materials are oils or oil-soluble. These may be isolated in a variety of ways. A first methodology is steam distillation, an ancient method in which the plant is exposed to hot water or vapor, leaving behind a liquid called an essential oil. This method is a desirable one, in that it uses no petrochemicals, but has some limitations, in that it is not useful in extracting essential oils from all types of plant matter. In particular, floral aroma components tend to be altered by the process, so that very few floral essential oils, which would be very much in demand as fragrance ingredients can be prepared in this manner.

A second method of obtaining fragrance components from plant materials is solvent extraction. This process typically employs a non-polar, petrochemical (hydrocarbon) solvent such as benzene, toluene or hexane, to dissolve the waxy and aromatic materials from the plants. The solvent is then evaporated off to leave a solid or semi-solid material known as a "concrete". The concrete is then washed with ethanol to dissolve the ethanol-soluble components, and with chilling, the waxes can then be filtered off. The ethanol is then evaporated under vacuum, leaving a material known as an "absolute". All three of these components, i.e., waxes, concretes and absolutes are widely used in the fragrance industry. The limitation of this method ties in its use of petrochemical solvents; many fragrance manufacturers, and particularly aromatherapists, are reluctant to use these products, because of the petrochemical solvent residue. Such residues may also hinder organic certification in those situation where such certification may be desirable.

Another method of obtaining natural fragrance ingredients is known as expression, where the fragrance component is expressed or squeezed out of the plant source. This method is frequently used to obtain natural oils from the peel of citrus fruits such as lemon, time or orange. However, it is not practical for application to delicate floral parts which are the source of so many desirable fragrance components.

A new method of extracting aroma ingredients is supercritical carbon dioxide. This involves heating and pressurizing $CO_2$ until it reaches the supercritical stage and using it as a solvent. It has the advantage of easy removal from the extract (it simply evaporates), but the water in fresh plant materials, such as leaves and flowers interferes with its solvency, making the process inefficient and resulting in poor quality extracts.

Thus, the present state of affairs in the fragrance industry is that there is no currently available method which can produce a variety of floral fragrance absolutes that can be certified organic. However, the present invention now provides such a useful method, along with aromatic components having a unique fragrance and chemical composition.

SUMMARY OF THE INVENTION

The present invention relates to a method for extracting aroma components from plant materials which comprises contacting the plant material containing aroma components with a volatile ester, preferably an ester of the general formula $CH_3COOR$, where $R{=}CH_3$, $C_2H_5$, $C_3H_7$, $C_4H_9$ or $C_5H_{11}$ for a period of time sufficient to achieve transfer of aroma components to the ester; separating the plant material and ester; evaporating the ester to produce a concrete containing aroma components; optionally contacting the concrete with at least one alcohol wash, chilling the wash to separate an alcohol soluble fraction from a wax fraction, isolating the wax fraction from the alcohol soluble fraction, and evaporating the alcohol from the alcohol soluble fraction to produce an absolute fraction. The invention also provides novel aromatic concrete, wax and absolute components that are produced by this method.

DETAILED DESCRIPTION OF THE INVENTION

The present invention provides a novel solvent extraction means for production of fragrance components. Unlike currently used solvent extraction methods, the present invention utilizes as its solvent an organic ester, particularly a volatile organic ester. By volatile in the present context is meant an ester having a boiling point no higher than about 130° C. Useful esters for the present purpose are represented by the formula $CH_3COOR$, where $R{=}CH_3$, $C_2H_5$, $C_3H_7$, $C_4H_9$ or $C_5H_{11}$. A particularly preferred ester for this purpose is ethyl acetate, because of its greater volatility (a boiling point of about 77° C., similar to the more traditional solvent used in this process). However, other esters of the noted formula, for example isobutyl acetate, which may have higher boiling points, can also provide the same result, but with somewhat greater effort required to remove the solvent, with the risk of loss of some top notes in the process.

Although ethyl acetate is of course a well known solvent which is frequently used in preparing extracts of plants for the isolation of biologically active materials, such as proteins, polysaccharides and the like, it has not, to the inventors' knowledge, previously been used in the isolation of fragrance components. Indeed, given the generally oily or non-polar characteristics of the bulk of fragrance components, it is somewhat counterintuitive to use a polar solvent such as ethyl acetate to extract these materials from plants. It does, however, not only effectively yield the same typical fractions of aroma materials as the non-polar solvent extraction, but it unexpectedly gives a substantially higher yield, up to two to three times that achieved with a traditional hexane extraction.

More importantly, the resultant fractions obtained are also of a very different character than those obtained with a hexane, toluene or benzene extraction, having different physical characteristics, being overall more aromatic, and having a different odor profile than the same fractions obtained with petrochemical solvent extraction. Of particular advantage is the fact that extracts made by this method can certified organic. Ethyl acetate is an organic ester obtainable by the reaction of two natural substances, ethyl alcohol and vinegar. Thus, aroma components isolated in this manner do not contain undesirable petrochemical residues that make other commercially available concretes, waxes or absolutes undesirable to a certain segment of the fragrance industry, and make them further unable to be certified as organic.

The method of extraction of the plant material is relatively straightforward. Plant material known to contain the aroma components of interest are gathered. These can be any portion of the plant, e.g., flowers, stems, leaves, or roots. Porous plant material, such as leaves and flowers, can be used whole or ground, while non-porous materials, such as nuts or seeds, must be ground before extraction. The plant material is then immersed in the ester solvent and allowed to reside together for a short period of time, as short as 15 seconds, but typically no more than five to ten minutes. Longer residence times of 30-60 minutes, which are more typical of a hexane-based process, result in the extraction of materials that may be incompatible with other aroma ingredients, such as certain essential oils. In this wash, the ratio of the solvent to plant material is not critical, and may be just enough to cover the plant material. As one example, however, if a relatively light material, such as flowers are being used, about 3 kilograms of solvent to every kilogram of plant material provides good results. The ratio can be altered depending on the density of the source material, so that with very dense materials, less solvent can be used, and with lighter material, more solvent may be used. Generally speaking, the use of more solvent results in the extraction of more material faster. However, there is no criticality in these amounts, as the only limitation is the ability to remove the solvent at the end of the process.

After immersion, the solvent fraction and the plant fraction of the mixture are then separated. Surprisingly, and unlike a hexane extraction, a large quantity of aromatic material can be extracted in the very short, single exposure as described above, and no further washes are necessary to obtain an acceptable yield. However, it is possible, if desired, to expose the plant fraction to a second solvent wash, again for no more than 5 minutes, this time with about a 2:1 ratio of solvent: plant, and the two fractions separated. Optionally, a third washing of the plant material is conducted, for a slightly longer period, e.g., at least about 10 minutes, with a solvent: plant ratio of about 1:1. If multiple washings are performed, these will be combined for the following steps. It should be noted, however, that there will not ordinarily be a very significant increase in yield with multiple washings, as the first washing extracts so much of the aromatic material.

After washing(s), the plant material is discarded, and then the solvent evaporated from the washing(s), leaving a concrete. The concrete is a mixture of waxes and aromatic materials, which can be used as-is (as can any waxes further purified from the concrete or the remaining extract) in cosmetic products, such as lipsticks or lotions, in the same manner as other waxes are used, to modify physical properties, such as viscosity or structure, but with the added advantage of providing aroma at the same time.

In an alternate embodiment, all or a portion of the concrete obtained can also be further treated to isolate the absolute and wax fractions, by washing at least once with alcohol, followed by chilling and filtration. A single wash will result in extraction of a significant portion of the aromatic material, but multiple washings, preferably at least two, will ordinarily increase the efficiency of the separation. Ethanol is the preferred alcohol for this stage, but the alcohol may be any monohydric or polyhydric alcohol, for example, isopropanol or propylene glycol, that is consistent with a cosmetic and/or fragrance end use of the final product. It is preferred that the alcohol used be relatively volatile; however, if the evaporation of the solvent is not essential for the intended end use, then a non-volatile solvent, such as glycerine, could also be used, on the understanding that the non-volatile material will significantly dilute the final absolute. A chilling step after the wash results in a separation out of a wax fraction, which can then be separated from the alcohol wash, for example by filtration. The resulting alcohol fraction is then evaporated off to produce the absolute, which may be optionally filtered to remove any remaining small solids. An exemplary procedure for this washing process is as follows: 10 parts of 200 proof alcohol is added for every part of concrete. The mixture is mixed with a propeller mixture at room temperature for about an hour, then chilled with slow mixing to −30° C. The mixture is filtered to clarity. The solid extract is then added back to the mixing vessel, and additional alcohol is added, typically about 8 parts alcohol to one part of solid extract. The mixing, chilling and filtering steps are repeated, then a third washing, with about 6 parts alcohol to one part solid extract, is performed. Those skilled in the art will readily recognize that the conditions of foregoing procedures are not necessarily critical, and can be modified, for example, as to residence time in solvent, ratio of solvent to material, number of washes, and the like; modifications may result in a difference in ultimate yield but will nonetheless result in qualitatively similar products at the end of the procedure.

The resulting fractions, i.e., concretes, waxes and absolutes are, as noted above, unexpectedly chemically distinct from a corresponding petrochemical solvent extract of the same material. Initial observations on the fragrance qualities of the absolutes by an expert perfumer showed a very distinct difference qualitatively between hexane derived extracts and ethyl acetate derived extracts. This suggested that perhaps there may be a chemical difference in the composition of the extracts as well. In order to confirm this hypothesis, the two types of extracts were subjected to a GC/MS analysis. The results, repeated with several different types of floral extracts, do in fact show that the chemical components of hexane extracts differ significantly from the ethyl acetate extracts. These differences are found both in proportions of components common in both, as well as the overall identity of the components in each. For example, with jasmine extracts, a total of 60 components are found between the two abstracts, with only seven being found in both extracts, and even in the case of commonly found components, these are found, in some cases, in vastly different amounts. A more detailed analysis of these experiments is provided in example 3 below. Another observation is that absolutes prepared in the manner of the present invention will typically show a lower indole content than the corresponding petrochemically isolated absolute. This can be quite important because the indole portion of a fragrance is also referred to the "animalic content", conveying a character to a fragrance that is specifically not desired in a high quality floral. In addition, similar tests show a higher benzyl acetate content in the hexane extraction.

Another distinction is the concentration of waxes obtained in this extraction procedure is significantly higher than that observed with the hexane extract. Because the waxes themselves have a cosmetic utility separate from that of the absolutes (i.e., any cosmetic or pharmaceutical use that waxes are normally put to), this provides an added efficiency to the process. In addition, the character of the waxes obtained is distinct: the waxes produced by the ethyl acetate process are generally darker and more aromatic than the typical hexane process waxes. Thus, the results observed confirm that each of the fractions obtained from the process is a unique product, chemically distinct from comparable fractions obtained by more traditional petrochemical-based extraction procedures.

The plant source for extraction can be any type of plant which is useful as a source of aroma components. These include, for example, fruits (strawberry, apple, melon, lemon, lime, orange, and grapefruit), herbs or leaves (e.g., tomato, basil, patchouli, citrus, sage, violet, rosemary or hay), seeds (e.g., coriander, caraway, cocoa, tonka, nutmeg, mace cardamom, and anise), spices (star anise, pepper, allspice), woods (e.g., birch, cedar, sandalwood, juniper, larch and pine), barks (e.g., cinnamon), roots (e.g., ginger, vetiver or iris) and flowers. It is particularly advantageous, however, when applied to flowers, because of the typical difficulty in obtaining good quality essential oils from flowers, combined with the great demand for floral components and the great expense associated with them. An essential oil is ordinarily defined as the oil obtained by steam distillation of a plant material. Peppermint, sandalwood, basil, and rose oils are all essential oils, obtained by steam distillation; in some cases, although not all, rose being a notable exception, the essential oils are the richest and most complex, and therefore, most important, aroma component of a particular plant. Many flowers, however, will not yield an essential oil by steam distillation. Jasmine is perhaps the best known of these flowers. Attempts at steam distillation of jasmine flowers results in a water condensate that smells nothing like the flowers, with no essential oil. The only way to get the aroma out of jasmine flowers is by extracting it with a solvent, which heretofore has always been petrochemical, and therefore unacceptable to some consumers. Advantageously, the present invention now for the first time provides the means by which an essential oil can be obtained from certain plant sources without the use of petrochemical solvents.

As an added benefit, the present method provides a greater yield of certain fractions. In comparable extractions, the yield of the concrete is significantly higher for the ethyl acetate concrete compared to the hexane concrete (see example 2 below). The yield of aromatic absolute is about the same for the ethyl acetate process as for the hexane process, so that the increase in the amount of concrete is represented in the higher amount of waxes that are extracted by the ethyl acetate. This is particularly unexpected, since waxes are generally nonpolar, and yet the present process extracts more of them with a solvent that is more polar than the petrochemical solvents, and with a shorter solvent residence time. In addition, the processing costs for achieving this result are substantially the same as those incurred with the use of hexane, thus in effect reducing the costs of the final products. Perhaps more importantly, however, the method also provides a means for getting organically certifiable floral fragrances, something that has heretofore not been achievable with more than a handful of floral sources, because of the damaging effects of steam distillation on floral oils. This more natural quality of the fragrance components can be an important feature both to perfumers as well as aromatherapists, and will also enhance the enjoyment of the fragrance by the ultimate consumer of the product. Examples of flowers that are sources of popular aroma components, and which will be useful in this extraction procedure include, but are not limited to rose, jasmine, orange blossom, carnation, geranium, mimosa, tuberose, violet, lavender, lilac, honeysuckle, blue chamomile, orchids and muguet. Although the present method is particularly important in isolating aroma components from flowers or floral parts, it will also be appreciated that it can be employed with any plant material containing aroma or wax components soluble in the volatile ester. Examples of other useful plant sources include trees, shrubs, herbs and vegetables, and the plant parts used for extraction may be any plant part, including, but not limited to, fruits, berries, leaves, stems, twigs, bark, wood, buds, seeds, roots, and pods. Examples of natural sources of fragrance components can be found, for example, in *Perfumery, Practice and Principles*, Calkin and Jellinek (1994), or *Perfumery and Flavoring Materials*, Bedoukian (1995), the contents of each being incorporated herein by reference.

The concretes, absolutes and waxes produced by the method can be used in a number of ways in fragranced products. Each can be used atone, in combination with each other, or in combination with one or more components appropriate to their intended end use, for example, for cosmetic or pharmaceutical use, with a topically acceptable carrier. Examples of products in which the components can be used are personal care products such as perfumes, colognes, fragranced body sprays and splashes; products for application to the hair, such as shampoos, conditioners, setting gels, hair sprays and the like; products for application to the skin, such as cosmetic creams, lotions, milks, sticks, glosses, gets and powders; or color cosmetics, such as lipsticks, lip glosses, foundations, blushes, eyeshadows, eyeliners or mascaras; home fragrance products, such as candles, room sprays, fragrance diffusers, wax tarts, incense, and the like; and aromatherapy products, such as fragranced massage oils. The preparation of such products is well known in the art; for example, formulations of cosmetic and pharmaceutical compositions are described in *Harry's Cosmeticology*, Eighth Edition, M. Reiger, ed. (2000), and *Remington: The Science and Practice of Pharmacy*, Twentieth Edition, A. Gennaro, ed., (2003) the contents of each of these being incorporated herein by reference. The components produced by the present method can be readily used in any such types of formulations in place of traditionally prepared components. The skilled artisan will readily recognize other applications of the aroma components produced by the present invention, and will further recognize that they can be used in any context in which traditional fragrance components can be used.

The invention is further illustrated by the following non-limiting examples.

Example 1

This Example Illustrates the Preparation of Aroma Components of Jasmine Flowers 25 kilos of jasmine flowers are packed into a wire basket and compressed, but not so much that a solvent cannot penetrate into and flow through them. The basket is immersed into a steam jacketed stainless steel tank containing just enough room-temperature (approximately 22-27° C.) ethyl acetate to cover the flowers completely. The combined components are not agitated After 15 seconds, the wire basket with jasmine flowers is removed from the solvent, the solvent is allowed to drain off for about one minute, and the flowers discarded. The extract solution is heated to 60-70° C. and mixed slowly until most of the ethyl acetate is removed. The evaporated ethyl acetate may be passed through a condenser and collected for re-use. When the extract is condensed to the point where it is about 50% ethyl acetate, the extract is chilled to minus 20° C. and the extract is held for at least 15 minutes, which precipitates out the bulk of the waxes, leaving an extract with some additional waxes, ethyl acetate and aroma compounds. A small amount (about 10% of the quantity of the extract) of 200 proof ethanol is added to the extract and mixed until uniform (approximately 15 minutes). The extract is added to a vacuum distillation unit and heated to 40-50° C. A moderate vacuum (20-100 mm mercury) is applied to remove the rest of the ethyl acetate. At this stage, the extract represents a concrete, minus some of the waxes that were initially removed.

The extract can then be transferred to a stainless steel jacketed tank and add 10 parts of 200 proof alcohol for every 1 part of extract, in order to separate aromatic components from waxes. The components are mixed with a propeller mixer at room temperature for 1 hour, then chilled with slow mixing to minus 30° C. The extract is filtered to clarity. The solid extract from the filter is added back to the tank and 8 parts of alcohol to 1 part solid extract is added. Mixing, chilling and filtering is repeated. A third time repetition of the washing, with 6 parts alcohol to 1 part extract, is then performed. Alcohol washings are placed in a vacuum distillation unit and warmed to 40-55° C. Moderate vacuum (20-100 mm mercury) is applied to remove alcohol. The final aromatic ethyl acetate absolute is the dark brown pasty material left after removal of the alcohol, while the remaining solid extract represents the wax fraction.

Example 2

One kilo of jasmine flowers is extracted by the traditional hexane process (3 washes at room temperature, 15 minutes soaking time each, then evaporate off the solvent) to produce approximately 2.5 grams of concrete. The concrete is then extracted with ethanol, similar to the procedure described above. The yield of absolute is approximately 1.3 grams.

One kilo of jasmine flowers is extracted with ethyl acetate by the process in example 1 to produce approximately 6 grams of concrete, the larger amount of concrete representing a higher level of waxes extracted by this process as opposed to the hexane process. The concrete is then further extracted with ethanol as per example 1 to produce approximately 1.2 grams of absolute, the remainder being waxes.

Example 3

This Example Illustrates the Qualitative and Quantitative Differences Between Hexane-Extracted and Ethyl Acetate-Extracted Absolutes Hexane and ethyl acetate absolutes of different flowers are prepared substantially as disclosed above in example 2. In a qualitative evaluation by an expert perfumer, a jasmine hexane absolute is found to have a rich, fine, sweet floral note, whereas the jasmine ethyl acetate absolute exhibits a light floral note with a less smooth sweetness. Similarly, violet leaves hexane absolute possesses a very fresh, light cucumber green note, whereas a violet leaves ethyl acetate absolute has a very heavy green note, similar to that of oakmoss, with no cucumber green.

These qualitative observations are followed by an evaluation of the quantitative differences between the absolutes produced by different extractions. The comparison is made by gas chromatography/mass spectrometry. The system consisted of an Agilent 6890N GC with a HP1MS (nonionic) column made by J&W, and an Agilent 5973 mass spectrometer. The runs are done with a temperature ramp of 4° C. per minute from 50° C. to 250° C.

Jasmine flowers, picked from the same fields and harvested at the same time, were extracted with hexane and ethanol or ethyl acetate and ethanol. A GC/MS analysis finds 60 compounds that can be identified and quantified. Of these, only seven are found in both absolutes; the other 54 are found in one absolute but not the other. All seven of the compounds common to both extracts (Benzyl Acetate, Benzyl Benzoate, Benzindan-1,2,2-trione 2-oxime, Isophytol, Palmitic Acid, Phytol and Dioctyl Phthalate) are found in significantly different concentrations in the two materials. For example, Benzyl Acetate is found in the hexane absolute at 16.99% but in the ethyl acetate absolute at only 0.98%. Benzyl Benzoate (another compound common to many flower essences) is in the hexane absolute at 12.6% but in the ethyl acetate absolute at only 0.46%. Thirty-four compounds are found in the hexane absolute only, and 20 compounds are found in the ethyl acetate absolute only.

A comparison of orange flower absolutes shows similar results. Fifty-eight compounds are identified. Nineteen are common to both absolutes, thirty-four are found only in the hexane absolute, and 5 are found only in the ethyl acetate absolute.

Violet leaves extracts show an even more dramatic difference. Of the 15 compounds found in the extracts, only one, Octadecadienoic Acid, is common to both. Eight compounds are found only in the hexane absolute, and 6 are found only in the ethyl acetate absolute. These results explain the dramatic differences observed in qualitative aroma profile, and also unequivocally show that the products of the two different extraction processes are chemically distinct entities.

What we claim is:

1. A method for extracting aroma components from plant materials which comprises immersing a plant material containing aroma components and selected from the group consisting of fruits, berries, flowers, leaves, stems, twigs, bark, wood, buds, seeds, roots, and pods in a volatile ester for a period of time of less than 30 minutes to achieve transfer of aroma components from the plant material to the ester, separating the ester containing aroma components from the plant material, and evaporating the ester to produce a concrete fraction containing waxes and aroma components; subjecting the concrete to at least one alcohol wash, in which the alcohol is ethanol, chilling the wash to separate an alcohol soluble fraction containing aroma components from a wax fraction, isolating the wax fraction from the alcohol soluble fraction, and evaporating the ethanol alcohol from the alcohol soluble fraction to produce an absolute fraction.

2. A method for extracting aroma components from plant materials which comprises immersing a plant material containing aroma components in a volatile ester for a period of time of less than 30 minutes to achieve transfer of aroma components from the plant material to the ester, separating the ester containing aroma components from the plant material, and evaporating the ester to produce a concrete fraction containing waxes and aroma components; optionally subjecting the concrete to at least one alcohol wash, chilling the wash to separate an alcohol soluble fraction containing aroma components from a wax fraction, isolating the wax fraction from the alcohol soluble fraction, and evaporating the alcohol from the alcohol soluble fraction to produce an absolute fraction, in which the plant material is a flower is selected from the group consisting of rose, jasmine, orange blossom, carnation, geranium, mimosa, tuberose, violet, lavender, lilac, honeysuckle, blue chamomile, orchid and muguet.

* * * * *